(12) United States Patent
Alanine et al.

(10) Patent No.: US 7,790,732 B2
(45) Date of Patent: Sep. 7, 2010

(54) 5-CHLORO-4-ALKYL-3,4-DIHYDRO-QUINAZOLIN-2-YLAMINE DERIVATIVES

(75) Inventors: Alexander Alanine, Schlierbach (FR); Luca Claudio Gobbi, Oberwil (CH); Sabine Kolczewski, Rheinfelden (DE); Thomas Luebbers, Loerrach (DE); Jens-Uwe Peters, Grenzach-Wyhlen (DE); Lucinda Steward, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 1113 days.

(21) Appl. No.: 11/472,081

(22) Filed: Jun. 21, 2006

(65) Prior Publication Data

US 2006/0293349 A1 Dec. 28, 2006

(30) Foreign Application Priority Data

Jun. 27, 2005 (EP) .................................. 05105697

(51) Int. Cl.
*A61K 31/517* (2006.01)
*C07D 239/84* (2006.01)

(52) U.S. Cl. .................................... 514/266.4; 544/292
(58) Field of Classification Search .............. 514/266.4; 544/292

See application file for complete search history.

(56) References Cited

U.S. PATENT DOCUMENTS

| 4,499,092 A | 2/1985 | Hallot et al. |
| 5,693,652 A * | 12/1997 | Takase et al. ............... 514/322 |
| 6,194,420 B1 | 2/2001 | Lang |

FOREIGN PATENT DOCUMENTS

| FR | 2 514 765 | 4/1983 |
| WO | WO 99/21850 A1 | 5/1999 |
| WO | WO 2004/096771 | 11/2004 |
| WO | WO 2006/117305 A1 | 11/2006 |

OTHER PUBLICATIONS

Rahman, A.A., et al., Bioorganic & Medicinal Chemistry Letters, Oxford, GB, vol. 13, No. 6, pp. 1119-1123 (2003), XP002298657.
Tsuang, M.T., et al., Journal of Psychiatric Research, Oxford, GB, vol. 38, No. 1, pp. 3-15 (2004), XP004785327.
Hoyer et al., Pharmacol. Rev. vol. 46, pp. 157-204 (1994).
Rees, S. et al., FEBS Letters, vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Dubertret C. et al., The Journal of Psychiatric Research, vol. 38, pp. 371-376 (2004).
Trinka et al., J. Prakt. Chem. vol. 338(7) pp. 675-678 (1996).

* cited by examiner

*Primary Examiner*—James O Wilson
*Assistant Examiner*—Tamthom N Truong
(74) *Attorney, Agent, or Firm*—George W. Johnston; Patricia S. Rocha-Tramaloni; Kimberly J. Prior

(57) ABSTRACT

The present invention relates to compounds of formula I

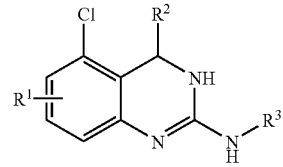

wherein
$R^1$, $R^2$, $R^3$ are as described in the specification and pharmaceutically acceptable acid addition salts and tautomers thereof.

Compounds of formula I have good activity on the 5-HT$_{5A}$ receptor. Therefore, the invention provides a method for treating diseases related to this receptor, for example, anxiety, depression, sleep disorders and schizophrenia.

24 Claims, No Drawings

5-CHLORO-4-ALKYL-3,4-DIHYDRO-QUINAZOLIN-2-YLAMINE DERIVATIVES

PRIORITY TO RELATED APPLICATIONS

This application claims the benefit of European Application No. 05105697.6, filed Jun. 27, 2005, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_{5A}$ serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP, and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders. The *Journal of Psychiatric Research*, 38, 371-376 (2004) describes evidence for a potential significant role of the 5-HT$_{5A}$ gene in schizophrenia and more specifically in patients with later age at onset.

SUMMARY OF THE INVENTION

The present invention provides compounds of formula I

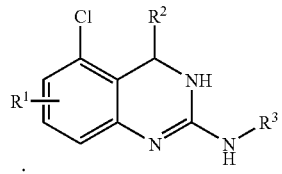

wherein
R$^1$ is hydrogen or halogen;
R$^2$ is lower alkyl;
R$^3$ is hydrogen, lower alkyl, —(CH$_2$)$_n$-cycloalkyl, —(CH$_2$)$_n$-phenyl optionally substituted by halogen, lower alkyl substituted by halogen, —(CH$_2$)$_n$-heterocyclyl, —(CH$_2$)$_n$N-di-lower alkyl, —(CH$_2$)$_n$NHC(O)-lower alkyl, adamantyl or —(CH$_2$)$_n$—O-lower alkyl; and
n is 0, 1, 2 or 3;

and pharmaceutically acceptable acid addition salts and tautomers thereof.

The compounds of formula I can contain asymmetric carbon atoms. Accordingly, the present invention includes all stereoisomeric forms of the compounds of formula I, including each of the individual enantiomers and mixtures thereof.

The present invention also provides pharmaceutical compositions containing one or more compound of the invention and a pharmaceutically acceptable carrier. The invention further provides methods for the preparation of such compounds and compositions.

Compounds of formula I are active on the 5-HT$_{5A}$ receptor. Therefore, the invention provides methods for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, schizophrenia, panic disorders, agoraphobia, social phobia, obsessive compulsive disorders, post-traumatic stress disorders, pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of general terms used herein apply irrespective of whether the terms in question appear alone or in combination. It should be noted that, as used in the specification and the appended claims, the singular forms "a," "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "cycloalkyl" denotes a saturated hydrocarbon ring containing from 3 to 7 carbon atoms, for example cyclopropyl, cyclopentyl, cyclohexyl and the like.

The term "O-lower alkyl" denotes a lower alkyl group as defined above, which is attached via an oxygen atom.

The term "heterocyclyl" denotes a cyclic group having one or two ring members, containing at least one heteroatom selected from the group consisting of N, O or S. Preferred groups are 2,3-dihydro-benzo[1,4]dioxin-2-yl, [1,4]dioxan-2-yl, pyridin-3-yl, piperidin-1-yl, 1-pyrrolidin-2-one, 2-(1H-imidazol-4-yl, and imidazolidin-2-one. The heterocyclyl group can be further substituted by lower alkyl.

The term "halogen" denotes chlorine, iodine, fluorine and bromine.

The term "lower alkyl substituted by halogen" denotes a lower alkyl group as defined above, wherein one or more hydrogen atoms is replaced by (a) halogen atom(s), for example $CH_2F$, $CHF_2$, $CF_3$, $CH_2CH_2F$, $CH_2CHF_2CH_2CF_3$ or the like.

The term "pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "therapeutically effective amount" means an amount that is effective to prevent, alleviate or ameliorate symptoms of disease or prolong the survival of the subject being treated.

The present invention provides compounds of formula I

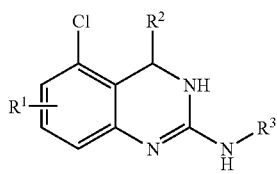

I wherein
$R^1$ is hydrogen or halogen;
$R^2$ is lower alkyl;
$R^3$ is hydrogen, lower alkyl, $-(CH_2)_n$-cycloalkyl, $-(CH_2)_n$-phenyl optionally substituted by halogen, lower alkyl substituted by halogen, $-(CH_2)_n$-heterocyclyl, $-(CH_2)_n$N-di-lower alkyl, $-(CH_2)_n$NHC(O)-lower alkyl, adamantyl or $-(CH_2)_n$-O-lower alkyl; and
n is 0, 1, 2 or 3;

and pharmaceutically acceptable acid addition salts and tautomers thereof.

The compounds of formula I can contain asymmetric carbon atoms. Accordingly, the present invention includes all stereoisomeric forms of the compounds of formula I, including each of the individual enantiomers and mixtures thereof.

Preferred compounds of formula I are those wherein $R^1$ is hydrogen. In particular, compounds wherein $R^1$ is hydrogen and $R^2$ is lower alkyl are preferred.

Preferred compounds of formula I are those, wherein $R^1$ is hydrogen and $R^2$ is methyl, for example the following compounds:
5-chloro-4-methyl-3,4-dihydro-quinazolin-2-ylamine,
(5-chloro-4-methyl-3,4-dihydro-quinazolin-2-yl)-methyl-amine,
(5-chloro-4-methyl-3,4-dihydro-quinazolin-2-yl)-cyclobutyl-amine and
(5-chloro-4-methyl-3,4-dihydro-quinazolin-2-yl)-(2,2-difluoro-ethyl)-amine.

Preferred compounds of formula I wherein $R^1$ is hydrogen are those wherein $R^3$ is hydrogen. Other such compounds are those wherein $R^3$ is lower alkyl. Still other such compounds are those wherein $R^3$ is lower alkyl substituted by halogen. Further compounds of formula I wherein $R^1$ is hydrogen are those wherein $R^3$ is $-(CH_2)_n$-cycloalkyl. Other such preferred compounds are those wherein $R^3$ is $-(CH_2)_n$-phenyl optionally substituted by halogen. Still other such preferred compounds are those wherein $R^3$ is $-(CH_2)_n$-heterocyclyl.

Preferred compounds of formula I wherein $R^1$ is hydrogen are further those wherein $R^3$ is $-(CH_2)_n$N-di-lower alkyl. Still other such compounds are those wherein $R^3$ is $-(CH_2)_n$NHC(O)-lower alkyl. Other preferred compounds where $R^1$ is hydrogen are those wherein $R^3$ is adamantyl. Further, such compounds are those wherein $R^3$ is $-(CH_2)_n$-O-lower alkyl.

Preferred compounds of formula I are those wherein $R^1$ is halogen, in particular those wherein $R^1$ is chloro. Other preferred compounds wherein $R^1$ is halogen are those wherein $R^2$ is methyl.

Preferred compounds of formula I are those, wherein $R^1$ is chloro and $R^2$ is methyl, for example the following compound:
5,6-dichloro-4-methyl-3,4-dihydro-quinazolin-2-ylamine,
(5,6-dichloro-4-methyl-3,4-dihydro-quinazolin-2-yl)-methyl-amine,
(5,6-dichloro-4-methyl-3,4-dihydro-quinazolin-2-yl)-(2,2-difluoro-ethyl)-amine,
cyclobutyl-(5,6-dichloro-4-methyl-3,4-dihydro-quinazolin-2-yl)-amine,
N-[2-(5,6-dichloro-4-methyl-3,4-dihydro-quinazolin-2-ylamino)-ethyl]-acetamide,
(5,6-dichloro-4-methyl-3,4-dihydro-quinazolin-2-yl)-pentyl-amine,
(5,6-dichloro-4-methyl-3,4-dihydro-quinazolin-2-yl)-(3-methoxy-propyl)-amine,
(5,6-dichloro-4-methyl-3,4-dihydro-quinazolin-2-yl)-[1,4]dioxan-2-ylmethyl-amine and
5,8-dichloro-4-methyl-3,4-dihydro-quinazolin-2-ylamine.

Among compounds wherein $R^1$ is chloro, those wherein $R^3$ is hydrogen are preferred. Other such preferred compounds are those wherein $R^3$ is lower alkyl. Still other such preferred compounds are those wherein $R^3$ is lower alkyl substituted by halogen. Further preferred compounds wherein $R^1$ is chloro are those wherein $R^3$ is $-(CH_2)_n$-cycloalkyl. Other such compounds wherein $R^3$ is $-(CH_2)_n$NHC(O)-lower alkyl are preferred.

Preferred compounds of formula I wherein $R^1$ is chloro are those wherein $R^3$ is adamantyl. Other such preferred compounds are those wherein $R^3$ is $-(CH_2)_n$-O-lower alkyl. Still other such preferred compounds are those wherein $R^3$ is $-(CH_2)_n$N-di-lower alkyl. Further such preferred compounds are those wherein $R^3$ is heterocyclyl.

Preferred compounds of formula I are those wherein $R^3$ is hydrogen. Other preferred compounds are those wherein $R^3$ is lower alkyl, in particular those wherein $R^3$ is methyl. Other preferred compounds of formula I are those wherein $R^3$ is lower alkyl substituted by halogen.

Preferred compounds of formula I are those wherein $R^3$ is $-(CH_2)_n$N-di-lower alkyl. Other preferred compounds are those wherein $-(CH_2)_n$-cycloalkyl. Still other preferred compounds are those wherein $R^3$ is adamantyl. Further preferred compounds are those wherein $R^3$ is $-(CH_2)_n$NHC(O)- lower alkyl. Preferred compounds also are those wherein $R^3$ is —$(CH_2)_n$-phenyl optionally substituted by halogen.

Preferred compounds of formula I are those wherein $R^3$ is —$(CH_2)_n$-heterocyclyl. Among these compounds, those wherein $R^3$ is piperidin-1-yl are preferred. Also preferred are those compounds wherein $R^3$ is 2-(1H-imidazol-4-yl) or imidazolidin-2-one. Other such preferred compounds are those wherein $R^3$ is [1,4]dioxan-2-yl. Still other preferred compounds are those wherein $R^3$ is 1-pyrrolidin-2-one. Further preferred compounds are those wherein $R^3$ is pyridin-3-yl. Preferred compounds of formula I are those wherein $R^3$ is 2,3-dihydro-benzo[1,4]dioxin-2-yl.

The present compounds of formula I and their pharmaceutically acceptable salts can be prepared by methods known in the art, for example by a process described below, which process comprises reacting a compound of formula

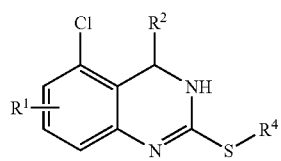

II with an amine of formula $R^3NH_2$  III to obtain a compound of formula

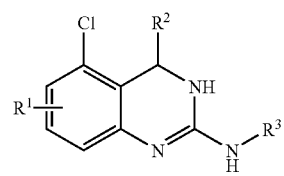

I wherein $R^1$, $R^2$ and $R^3$ are as described above and $R^4$ is lower alkyl, and if desired, converting the compounds obtained into pharmaceutically acceptable acid addition salts.

In examples 1-43 and in the following scheme 1 the preparation of compounds of formula I is described in more detail. The starting materials are known compounds or can be prepared according to methods known in the art.

Compounds of formula I can be prepared in accordance with the following scheme 1:

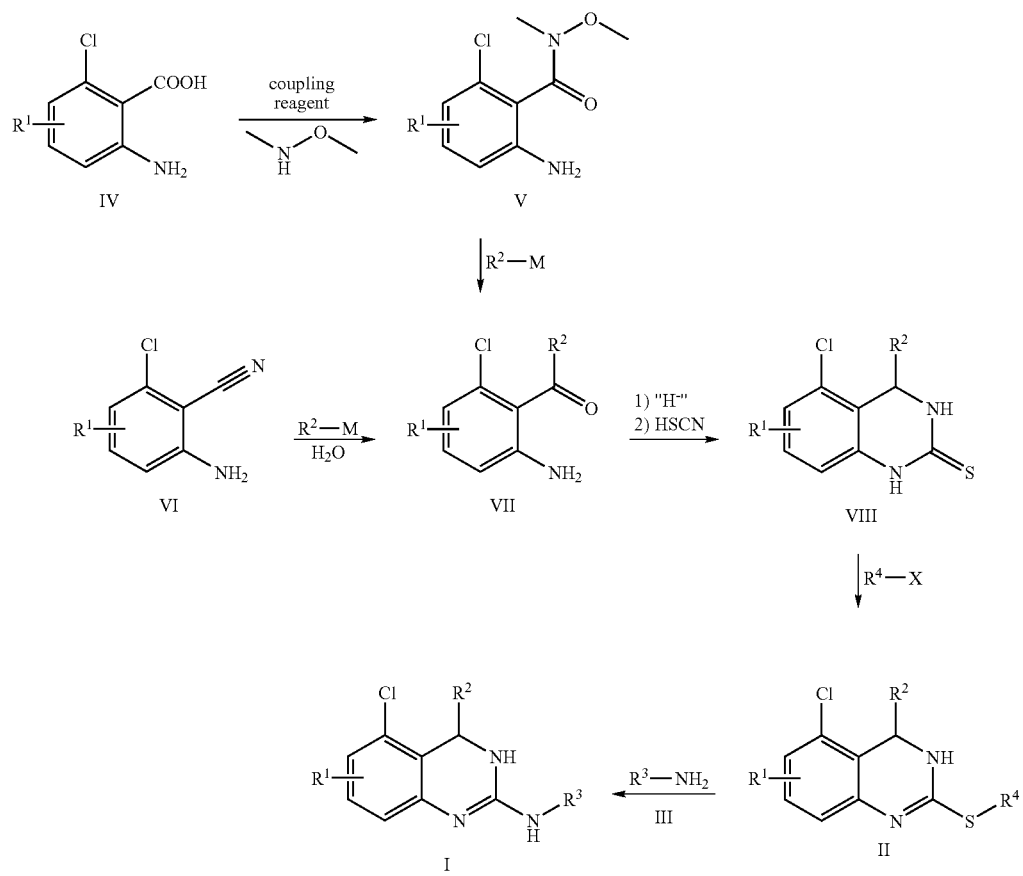

The substituents are as described above, $R^4$ is lower alkyl and X is halogen.

An 1-(2-amino-6-chloro-phenyl)-alkanone VII is reacted with a hydride transfer reagent ("H$^-$"), such as sodium borohydride, in a suitable solvent, such as ethanol, to give an intermediate which can be transformed by HSCN (which can be generated in situ from thiocyanate salt, e.g. KSCN, and an acid, e.g. HCl) to the cyclic thiourea VIII. VIII is reacted with the alkylating agent $R^4$—X, such as methyl iodide, in a suitable solvent, such as acetone, to give an 2-alkylsulfanyl-3,4-dihydro-quinazoline II, which can usually be isolated as a hydroiodide salt from the reaction mixture by filtration. II is then heated with the amine $R^3$—$NH_2$ in a suitable solvent, such as acetonitrile, in a microwave oven. 5-Chloro-4-alkyl-3,4-dihydro-quinazolin-2-ylamine I can then be isolated from the reaction mixture by conventional purification.

1-(2-amino-6-chloro-phenyl)-alkanones VII can be prepared in several ways. In one method, a substituted 2-amino-6-chloro-benzoic acid IV is suitably activated, for instance with a coupling reagent such as HBTU, and converted with N,O-dimethylhydroxylamine in a suitable solvent, such as DMF, and optionally in the presence of a base, such as N-methylmorpholine, to a Weinreb amide of formula V. After isolation and purification by conventional means, V is then converted with a metalloorganic reagent $R^2$-M, such as alkyllithium, in a suitable solvent, such as THF, for instance by allowing the reaction mixture to warm from low temperature, e.g. −78° C., to room temperature. Conventional workup and purification then gives a 1-(2-amino-6-chloro-phenyl)-alkanone VII. In another method, 1-(2-amino-6-chloro-phenyl)-alkanones VII are prepared by the reaction of a (substituted) 2-amino-6-chlorobenzonitrile VI with a metalloorganic reagent $R^2$-M, such as alkylmagnesium bromide, in a suitable solvent, such as diethyl ether, and subsequent hydrolysis under acidic conditions, for instance by addition of HCl.

The following abbreviations have been used:

HBTU=O-Benzotriazol-1-yl-N,N,N',N'-tetramethyluronium hexafluorophosphate

DMF=N,N-dimethylformamide

THF=tetrahydrofuran

M=metalloorganic group

Test Description

A [$^3$H] LSD radioligand binding assay was used to determine the affinity of the compounds for the recombinant human 5-$HT_{5A}$ receptor in membranes from transiently (cDNA) expressed 5-$HT_{5A}$ receptors in Human Embryonic Kidney-EBNA (HEK-EBNA) cells. Assay buffer consisted of Tris (50 mM) buffer containing 1 mM EGTA, 10 mM $MgCl_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. $IC_{50}$ values were calculated using a non-linear curve fitting program, and Ki values were calculated using the Cheng-Prussoff equation.

The activity of representative compounds (Ki≦0.02 µM) is described in the table below:

| Example | Ki (µM) |
|---|---|
| 1 | 0.00513 |
| 2 | 0.01082 |
| 3 | 0.01548 |
| 5 | 0.01013 |
| 8 | 0.002 |
| 9 | 0.00634 |
| 10 | 0.00567 |
| 15 | 0.0069 |
| 16 | 0.00887 |
| 18 | 0.01393 |
| 19 | 0.0069 |
| 21 | 0.01781 |
| 23 | 0.00585 |

The present invention also provides pharmaceutical compositions which comprise one or more compound of the invention and a pharmaceutically acceptable carrier. Such pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injectable solutions.

The compositions of the invention, in addition to one or more compounds of the invention, contain a pharmaceutically acceptable carrier. Suitable pharmaceutically acceptable carriers are pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the production of such pharmaceutical compositions. This process which comprises bringing one or more compounds of formula I and/or pharmaceutically acceptable acid addition salts and, if desired, one or more other therapeutically valuable substances into a galenical administration form together with one or more therapeutically inert carriers.

As mentioned earlier, the compounds of formula I and their pharmaceutically acceptable addition salts possess valuable pharmaceutical properties. Compounds of the present invention are active on the 5-$HT_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

|      |                        | mg/tablet |        |        |        |
| ---- | ---------------------- | --------- | ------ | ------ | ------ |
| Item | Ingredients            | 5 mg      | 25 mg  | 100 mg | 500 mg |
| 1.   | Compound of formula I  | 5         | 25     | 100    | 500    |
| 2.   | Lactose Anhydrous DTG  | 125       | 105    | 30     | 150    |
| 3.   | Sta-Rx 1500            | 6         | 6      | 6      | 30     |
| 4.   | Microcrystalline Cellulose | 30    | 30     | 30     | 150    |
| 5.   | Magnesium Stearate     | 1         | 1      | 1      | 1      |
|      | Total                  | 167       | 167    | 167    | 831    |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|      |                       | mg/capsule |       |        |        |
| ---- | --------------------- | ---------- | ----- | ------ | ------ |
| Item | Ingredients           | 5 mg       | 25 mg | 100 mg | 500 mg |
| 1.   | Compound of formula I | 5          | 25    | 100    | 500    |
| 2.   | Hydrous Lactose       | 159        | 123   | 148    | —      |
| 3.   | Corn Starch           | 25         | 35    | 40     | 70     |
| 4.   | Talc                  | 10         | 15    | 10     | 25     |
| 5.   | Magnesium Stearate    | 1          | 2     | 2      | 5      |
|      | Total                 | 200        | 200   | 300    | 600    |

Manufacturing Procedure

1. Mix items 1, 2 and 3 in a suitable mixer for 30 minutes.
2. Add items 4 and 5 and mix for 3 minutes.
3. Fill into a suitable capsule.

Compounds of formula I may be prepared as shown in the following description:

Example 1

5-Chloro-4-methyl-3,4-dihydro-quinazolin-2-ylamine

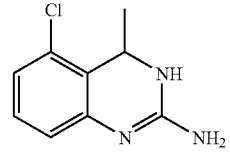

a) 1-(2-Amino-6-chloro-phenyl)-ethanone

A suspension of 2-amino-6-chlorobenzonitrile (3.67 g, 24 mmol) in diethyl ether (60 ml) was added slowly to methylmagnesium bromide (56 ml, 3 M in $Et_2O$, 170 mmol), and the mixture was heated to reflux, until all starting material was consumed (3 h, HPLC control). The mixture was then placed in an ice bath, and HCl (6M, 58 ml) was slowly added (vigorous reaction). The mixture was then again heated to reflux, cooled and made alkaline by addition of solid $Na_2CO_3$. The mixture was extracted several times with ethyl acetate, the combined organic phases were dried ($Na_2SO_4$), and the solvent was evaporated under reduced pressure. Purification of the residue by column chromatography (silica gel, solvent gradient n-heptan/ethyl acetate=100/0–60/40) gave the title compound (2.72 g, 67%). $^1$H NMR ($CDCl_3$): δ 2.65 (3H, s), 4.91 (2H, bs), 6.58 (1H, d), 6.73 (1H, d), 7.07 (1H, t).

b) 5-Chloro-4-methyl-3,4-dihydro-1H-quinazoline-2-thione

At a temperature of 65° C., sodium borohydride was added to a solution of 1-(2-amino-6-chloro-phenyl)-ethanone in ethanol, and the mixture was heated overnight (65° C.). Water, KSCN and HCl were then added subsequently, and the mixture was again heated (3 h, 65° C.). The majority of the title compound precipitated upon cooling and could be isolated in sufficiently pure form by filtration. A small additional amount of the desired product was obtained by workup of the mother liquor (evaporation of solvent, column chromatography [silica gel, solvent gradient n-heptan/ethyl acetate=100/0–60/40]). The title compound was obtained in a combined yield of 1.46 g (43%).

$^1$H NMR ($d^6$-DMSO): δ 1.26 (3H, d), 4.58 (1H, q), 6.97 (1H, d), 7.09 (1H, d), 7.23 (1H, t), 8.99 (1H, bs), 10.73 (1H, bs).

c) 5-Chloro-4-methyl-2-methylsulfanyl-3,4-dihydro-quinazoline hydroiodide

Methyl iodide (1.16 ml, 19 mmol) was added to a suspension of 5-chloro-4-methyl-3,4-dihydro-1H-quinazoline-2-thione (1.32 g, 6.2 mmol) in acetone (15 ml), and the mixture was stirred at r.t. over the weekend (the reaction is usually complete after 12 h). The precipitated product (2.08 g, 87%) was sufficiently pure for the next step.

$^1$H NMR ($d^6$-DMSO): δ 1.42 (3H, d), 2.76 (3H, s), 4.97 (1H, q), 7.11-7.14 (1H, m), 7.39-7.43 (2H, m), 10.58 (1H, bs), 12.38 (1H, bs).

d)
5-Chloro-4-methyl-3,4-dihydro-quinazolin-2-ylamine

5-Chloro-4-methyl-2-methylsulfanyl-3,4-dihydro-quinazoline hydroiodide (100 mg, 0.28 mmol) was suspended in a mixture of ammonium hydroxide (1 ml, 25% in H$_2$O) and acetonitrile (1 ml) and heated in a microwave oven to 130° C. (15 min) and subsequently to 170° C. (30 min). The title compound (35 mg, 62%) was isolated from the reaction mixture by preparative, reverse-phase HPLC (YMC Combi-Prep C18 column 50×20 mm, solvent gradient 5-95% CH$_3$CN in 0.1% TFA(aq) over 6.0 min, λ=230 nm, flow rate 40 ml/min) as a white solid.

$^1$H NMR (CDCl$_3$): δ 1.35 (3H, d), 4.83 (1H, q), 6.85 (1H, d), 6.92 (1H, d), 7.06 (3H, t).

Example 2

(5-Chloro-4-methyl-3,4-dihydro-quinazolin-2-yl)-methyl-amine

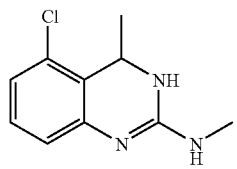

The title compound (MS: m/e=209.9 [M+H$^+$]) was prepared in analogy to example 1 from methylamine.

Example 3

(5-Chloro-4-methyl-3,4-dihydro-quinazolin-2-yl)-cyclobutyl-amine

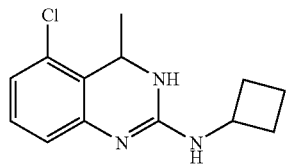

The title compound (MS: m/e=250.1 [M+H$^+$]) was prepared in analogy to example 1 from cyclobutylamine.

Example 4

(5-Chloro-4-methyl-3,4-dihydro-quinazolin-2-yl)-(2,2,2-trifluoro-ethyl)-amine

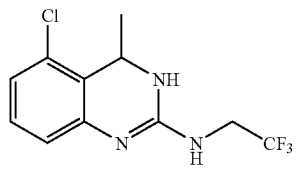

The title compound (MS: m/e=278.3 [M+H$^+$]) was prepared in analogy to example 1 from 2,2,2-trifluoroethylamine.

Example 5

(5-Chloro-4-methyl-3,4-dihydro-quinazolin-2-yl)-(2,2-difluoro-ethyl)-amine

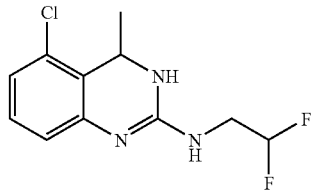

The title compound (MS: m/e=260.3 [M+H$^+$]) was prepared in analogy to example 1 from 2,2-difluoroethylamine.

Example 6

N'-(5-Chloro-4-methyl-3,4-dihydro-quinazolin-2-yl)-N,N-diisopropyl-ethane-1,2-diamine

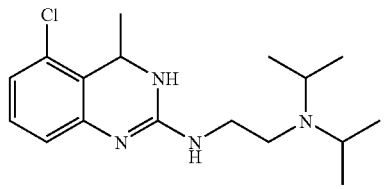

The title compound (MS: m/e=323.1 [M+H$^+$]) was prepared in analogy to example 1 from N,N-diisopropyl-ethane-1,2-diamine.

Example 7

(5-Chloro-4-methyl-3,4-dihydro-quinazolin-2-yl)-(2,3-dihydro-benzo[1,4]dioxin-2-ylmethyl)-amine

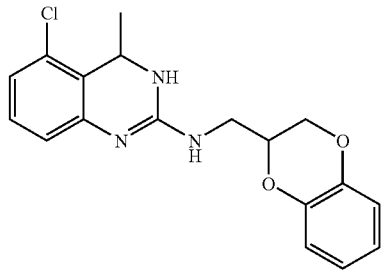

The title compound (MS: m/e=344.0 [M+H$^+$]) was prepared in analogy to example 1 from 2,3-dihydro-benzo[1,4]dioxin-2-ylmethyl-amine.

Example 8

5,6-Dichloro-4-methyl-3,4-dihydro-quinazolin-2-ylamine

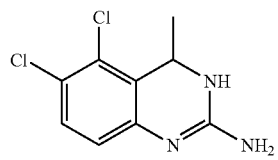

The title compound (MS: m/e=230.1 [M+H$^+$]) was prepared in analogy to example 1 from 2-amino-5,6-dichlorobenzonitrile. 2-Amino-5,6-dichlorobenzonitrile can be prepared by the method of Trinka, P.; Slegel, P.; Reiter, J. *J. Prakt. Chem.* 1996, 338(7), 675-678.

Example 9

(5,6-Dichloro-4-methyl-3,4-dihydro-quinazolin-2-yl)-methyl-amine

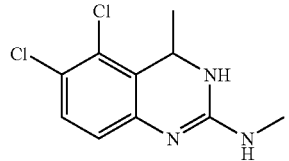

The title compound (MS: m/e=244.1 [M+H$^+$]) was prepared in analogy to example 1 from 2-amino-5,6-dichlorobenzonitrile and methylamine.

Example 10

(5,6-Dichloro-4-methyl-3,4-dihydro-quinazolin-2-yl)-(2,2-difluoro-ethyl)-amine

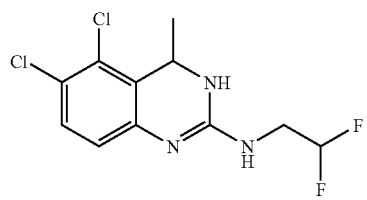

The title compound (MS: m/e=293.9 [M+H$^+$]) was prepared in analogy to example 1 from 2-amino-5,6-dichlorobenzonitrile and 2,2-difluoroethylamine.

Example 11

5-Chloro-4-ethyl-3,4-dihydro-quinazolin-2-ylamine

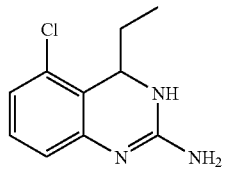

The title compound (MS: m/e=210.1 [M+H$^+$]) was prepared in analogy to example 1 from ethylmagnesium bromide.

Example 12

5,6-Dichloro-4-ethyl-3,4-dihydro-quinazolin-2-ylamine

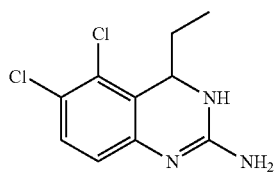

The title compound (MS: m/e=244.1 [M+H$^+$]) was prepared in analogy to example 1 from 2-amino-5,6-dichlorobenzonitrile and ethylmagnesium bromide.

Example 13

(5,6-Dichloro-4-ethyl-3,4-dihydro-quinazolin-2-yl)-methyl-amine

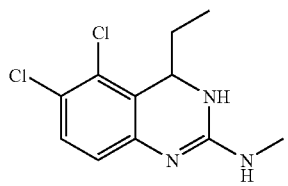

The title compound (MS: m/e=258.0 [M+H$^+$]) was prepared in analogy to example 1 from 2-amino-5,6-dichlorobenzonitrile, ethylmagnesium bromide, and methylamine.

Example 14

(5,6-Dichloro-4-ethyl-3,4-dihydro-quinazolin-2-yl)-(2,2-difluoro-ethyl)-amine

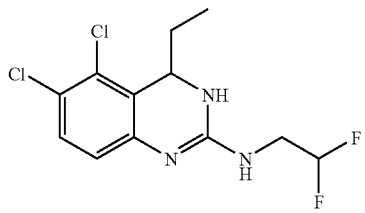

The title compound (MS: m/e=308.1 [M+H⁺]) was prepared in analogy to example 1 from 2-amino-5,6-dichlorobenzonitrile, ethylmagnesium bromide, and 2,2-difluoroethylamine.

Example 15

Cyclobutyl-(5,6-dichloro-4-methyl-3,4-dihydro-quinazolin-2-yl)-amine

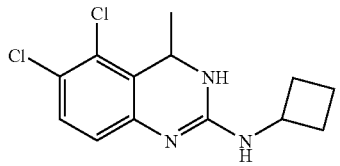

The title compound was prepared in analogy to example 1 from 2-amino-5,6-dichlorobenzonitrile and cyclobutylamine.

$^1$H NMR (CDCl$_3$): δ 1.08 (3H, d), 1.52-1.58 (2H, m), 1.73-1.77 (2H, d), 2.11-2.17 (2H, d), 4.17 (1H, tt), 4.55 (1H, q), 6.27 (1H, bs), 6.37 (1H, bs), 6.57 (1H, d), 7.13 (1H, d).

Example 16

N-[2-(5,6-Dichloro-4-methyl-3,4-dihydro-quinazolin-2-ylamino)-ethyl]-acetamide

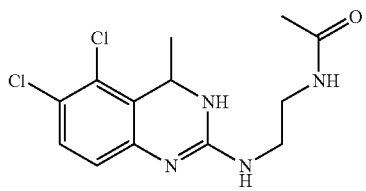

The title compound (MS: m/e=316.9 [M+H⁺]) was prepared in analogy to example 1 from 2-amino-5,6-dichlorobenzonitrile and N-(2-amino-ethyl)-acetamide.

Example 17

Adamantan-1-ylmethyl-(5,6-dichloro-4-methyl-3,4-dihydro-quinazolin-2-yl)-amine

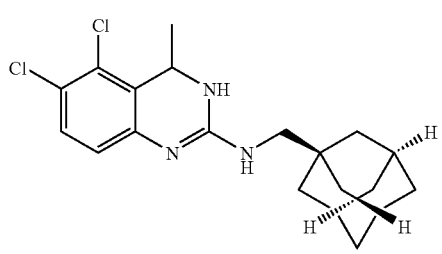

The title compound (MS: m/e=378.3 [M+H⁺]) was prepared in analogy to example 1 from 2-amino-5,6-dichlorobenzonitrile and adamantan-1-yl-methylamine.

Example 18

(5,6-Dichloro-4-methyl-3,4-dihydro-quinazolin-2-yl)-pentyl-amine

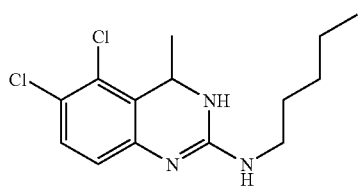

The title compound (MS: m/e=300.3 [M+H⁺]) was prepared in analogy to example 1 from 2-amino-5,6-dichlorobenzonitrile and pentylamine.

Example 19

(5,6-Dichloro-4-methyl-3,4-dihydro-quinazolin-2-yl)-(3-methoxy-propyl)-amine

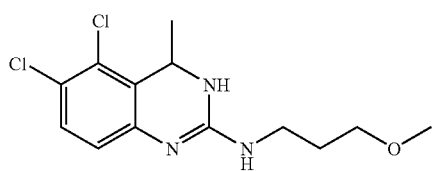

The title compound (MS: m/e=303.2 [M+H⁺]) was prepared in analogy to example 1 from 2-amino-5,6-dichlorobenzonitrile and 3-methoxy-propylamine.

Example 20

N'-(5,6-Dichloro-4-methyl-3,4-dihydro-quinazolin-2-yl)-N,N-diisopropyl-ethane-1,2-diamine

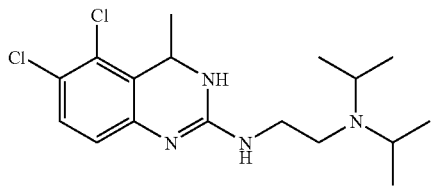

The title compound (MS: m/e=357.3 [M+H$^+$]) was prepared in analogy to example 1 from 2-amino-5,6-dichlorobenzonitrile and N,N-diisopropyl-ethane-1,2-diamine.

Example 21

(5,6-Dichloro-4-methyl-3,4-dihydro-quinazolin-2-yl)-[1,4]dioxan-2-ylmethyl-amine

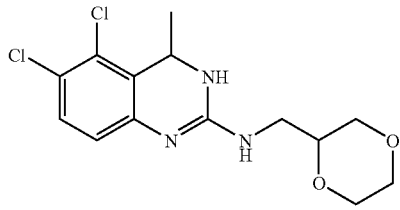

The title compound (MS: m/e=330.2 [M+H$^+$]) was prepared in analogy to example 1 from 2-amino-5,6-dichlorobenzonitrile and [1,4]dioxan-2-yl-methylamine.

Example 22

(5,6-Dichloro-4-methyl-3,4-dihydro-quinazolin-2-yl)-(2,3-dihydro-benzo[1,4]dioxin-2-ylmethyl)-amine

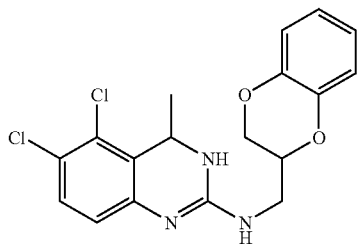

The title compound (MS: m/e=378.1 [M+H$^+$]) was prepared in analogy to example 1 from 2-amino-5,6-dichlorobenzonitrile and 2,3-dihydrobenzo[1,4]dioxin-2-ylmethylamine.

Example 23

5,8-Dichloro-4-methyl-3,4-dihydro-quinazolin-2-ylamine

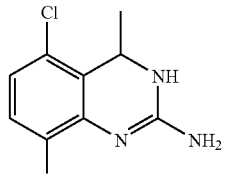

a)
2-Amino-3,6-dichloro-N-methoxy-N-methyl-benzamide

N,O-dimethlyhydroxylamine hydrochloride (3.28 g, 33 mmol) and 2-amino-3,6-dichlorobenzoic acid (4.76 g, 22 mmol) were dissolved in DMF (110 ml). At r.t. under nitrogen and stirring, first N-methyl morpholine (10 g, 99 mmol) and then HBTU (12.5 g, 33 mmol) were added, and the reaction was stirred at r.t. overnight. The reaction was poured onto water and extracted twice with ethyl acetate. The organic layer was dried over sodium sulfate, filtered, and the solvent was evaporated. The residue was treated with heptane and little diethyl ether to yield 4 g of the product. The mother liquor was purified by column chromatography (silica gel, solvent gradient n-heptan/ethyl acetate=3/7) to give another batch of the title compound as an off-white solid (5.52 g, 100%).

$^1$H NMR (d$^6$-DMSO): δ 3.29 (3H, s), 3.50 (3H, s), 5.43 (2H, bs), 6.69 (1H, d), 7.26 (1H, d).

b) 1-(2-Amino-3,6-dichloro-phenyl)-ethanone

At −78° C. a solution of methyl lithium (1.6M in diethyl ether, 25 ml, 40 mmol) was added dropwise to a solution of 2-amino-3,6-dichloro-N-methoxy-N-methyl-benzamide (2.5 g, 10 mmol) in tetrahydrofurane (100 ml). After complete addition, the reaction was warmed to r.t. The dark solution was stirred for 3 hours at room temperature. Under ice cooling 2N aqueous hydrochloride solution (25 ml) was added dropwise and stirred at r.t. for 30 minutes. The reaction was diluted with water, extracted twice with ethyl acetate. The combined organic layers were washed with saturated aqueous sodium chloride solution, dried over sodium sulfate, filtered, and the solvent was evaporated. The residue was purified by column chromatography (silica gel, solvent gradient n-heptan/ethyl acetate=3/7) to yield the title compound as an orange oil (0.59 g, 29%).

$^1$H NMR (CDCl$_3$): δ 2.65 (3H, s), 5.32 (2H, bs), 6.69 (1H, d), 7.21 (1H, d).

c) 5,8-Dichloro-4-methyl-3,4-dihydro-1H-quinazoline-2-thione

At a temperature of 65° C., sodium borohydride (0.13 g, 3.4 mmol) was added to a solution of 1-(2-amino-3,6-dichloro-phenyl)-ethanone (1.16 g, 5.7 mmol) in ethanol (12 ml), and the mixture was heated overnight (65° C.). Water (14.4 ml), KSCN (0.61 g, 6.3 mmol) and concentrated aqueous hydrogen chloride solution (3.6 ml) were then added subsequently, and the mixture was again heated (3 h, 65° C.).

The majority of the title compound precipitated upon cooling and could be isolated in pure form by filtration and washing with water and ethanol to yield a light yellow solid (0.96 g, 69%).

$^1$H NMR (CDCl$_3$): δ 1.56 (3H, d), 4.85 (1H, mq), 7.02 (1H, bs), 7.05 (1H, d), 7.25 (1H, d), 8.22 (1H, bs).

MS (EI): m/e=245.8/248.0 [M$^+$]

d) 5,8-Dichloro-4-methyl-2-methylsulfanyl-3,4-dihydro-quinazoline hydro iodide

Methyl iodide (0.73 ml, 11.7 mmol) was added to a suspension of 5,8-dichloro-4-methyl-3,4-dihydro-1H-quinazoline-2-thione (0.96 g, 3.9 mmol) in acetone (12 ml), and the mixture was stirred at room temperature overnight. The reaction was diluted with diethyl ether, and the precipitated product (1.31 g, 86%) was isolated by filtration as a white solid.

$^1$H NMR (d$^6$-DMSO): δ 1.29 (3H, d), 2.63 (3H, s), 4.81 (1H, q), 7.25 (1H, d), 7.46 (1H, d).

MS: m/e=261.0/263.0 [M+H$^+$].

e) 5,8-Dichloro-4-methyl-3,4-dihydro-quinazolin-2-ylamine 5,8-Dichloro-4-methyl-2-methylsulfanyl-3,4-dihydro-quinazoline hydroiodide (116 mg, 0.30 mmol) was suspended in a mixture of ammonium hydroxide (0.22 ml, 25% in H$_2$O, 3 mmol) and acetonitrile (0.9 ml), and heated in a microwave oven to 170° C. (30 min). The reaction was cooled in an ice bath and treated with 1N aqueous sodium hydroxide solution (0.9 ml) and 5-6 drops of concentrated solution of aqueous hydrogen peroxide. A little water was added, and the title compound (36 mg, 52%) was filtered off as a white solid.

$^1$H NMR (d$^6$-DMSO): δ 1.07 (3H, d), 4.54 (1H, mq), 5.96 (2H, bs), 6.57 (1H, bs), 6.67 (1H, d), 7.07 (1H, d).

MS: m/e=230.1/232.0 [M+H$^+$].

Example 24

Cyclobutyl-(5,8-dichloro-4-methyl-3,4-dihydro-quinazolin-2-yl)-amine

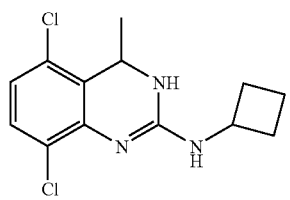

The title compound (MS: m/e=284.1/286.1 [M+H$^+$]) was prepared in analogy to example 23 from cyclobutyl amine.

Example 25

(5,8-Dichloro-4-methyl-3,4-dihydro-quinazolin-2-yl)-(2,2-difluoro-ethyl)-amine

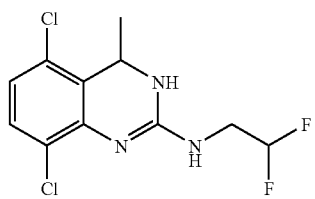

The title compound (MS: m/e=294.1/296.2 [M+H$^+$]) was prepared in analogy to example 23 from 2,2-difluoroethyl amine.

Example 26

(5-Chloro-4-methyl-3,4-dihydro-quinazolin-2-yl)-phenethyl-amine

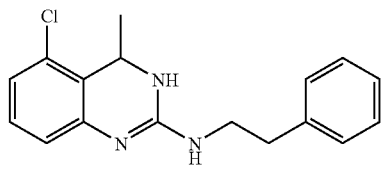

The title compound (MS: m/e=300.2 [M+H$^+$]) was prepared in analogy to example 1 from phenethylamine.

Example 27

(5-Chloro-4-methyl-3,4-dihydro-quinazolin-2-yl)-(3-phenyl-propyl)-amine

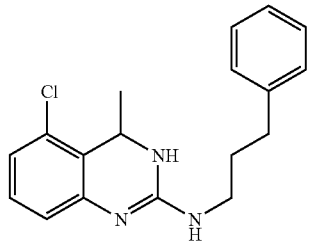

The title compound (MS: m/e=314.1 [M+H$^+$]) was prepared in analogy to example 1 from 3-phenyl-propylamine.

Example 28

(5-Chloro-4-methyl-3,4-dihydro-quinazolin-2-yl)-(2-methoxy-ethyl)-amine

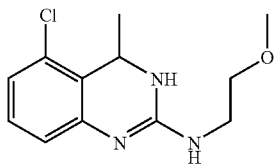

The title compound (MS: m/e=254.2 [M+H$^+$]) was prepared in analogy to example 1 from 2-methoxy-ethylamine.

Example 29

(5-Chloro-4-methyl-3,4-dihydro-quinazolin-2-yl)-pyridin-3-ylmethyl-amine

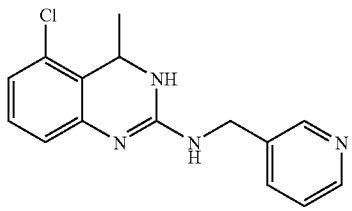

The title compound (MS: m/e=287.2 [M+H$^+$]) was prepared in analogy to example 1 from C-pyridin-3-yl-methylamine.

Example 30

(5-Chloro-4-methyl-3,4-dihydro-quinazolin-2-yl)-ethyl-amine

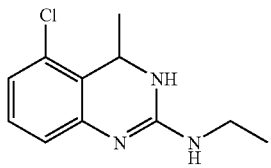

The title compound (MS: m/e=224.2 [M+H$^+$]) was prepared in analogy to example 1 from ethylamine.

Example 31

(5-Chloro-4-methyl-3,4-dihydro-quinazolin-2-yl)-cyclopropylmethyl-amine

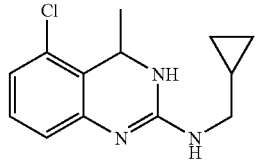

The title compound (MS: m/e=250.2 [M+H$^+$]) was prepared in analogy to example 1 from C-cyclopropyl-methylamine.

Example 32

N-[2-(5-Chloro-4-methyl-3,4-dihydro-quinazolin-2-ylamino)-ethyl]-acetamide

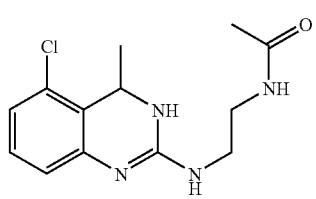

The title compound (MS: m/e=281.2 [M+H$^+$]) was prepared in analogy to example 1 from N-(2-amino-ethyl)-acetamide.

Example 33

Butyl-(5-chloro-4-methyl-3,4-dihydro-quinazolin-2-yl)-amine

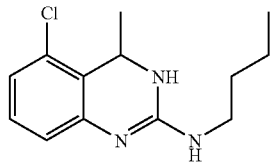

The title compound (MS: m/e=252.2 [M+H$^+$]) was prepared in analogy to example 1 from butylamine.

Example 34

(5-Chloro-4-methyl-3,4-dihydro-quinazolin-2-yl)-[2-(4-fluoro-phenyl)-ethyl]-amine

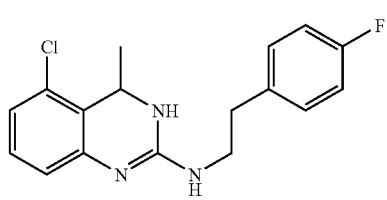

The title compound (MS: m/e=318.0 [M+H⁺]) was prepared in analogy to example 1 from 2-(4-fluoro-phenyl)-ethylamine.

Example 35

(5-Chloro-4-methyl-3,4-dihydro-quinazolin-2-yl)-(2-piperidin-1-yl-ethyl)-amine

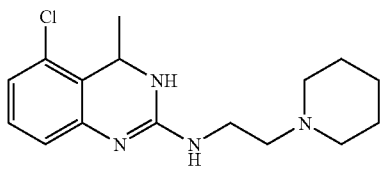

The title compound (MS: m/e=307.3 [M+H⁺]) was prepared in analogy to example 1 from 2-piperidin-1-yl-ethylamine.

Example 36

(5-Chloro-4-methyl-3,4-dihydro-quinazolin-2-yl)-(3-methoxy-propyl)-amine

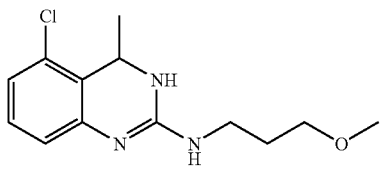

The title compound (MS: m/e=268.2 [M+H⁺]) was prepared in analogy to example 1 from 3-methoxy-propylamine.

Example 37

(5-Chloro-4-methyl-3,4-dihydro-quinazolin-2-yl)-isobutyl-amine

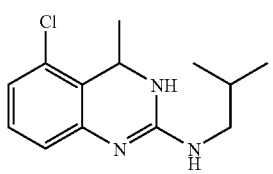

The title compound (MS: m/e=252.2 [M+H⁺]) was prepared in analogy to example 1 from isobutylamine.

Example 38

1-[3-(5-Chloro-4-methyl-3,4-dihydro-quinazolin-2-ylamino)-propyl]-pyrrolidin-2-one

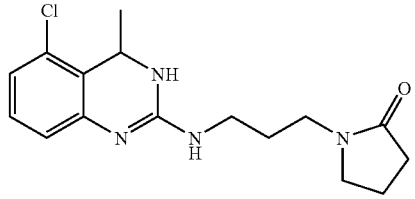

The title compound (MS: m/e=321.1 [M+H⁺]) was prepared in analogy to example 1 from 1-(3-amino-propyl)-pyrrolidin-2-one.

Example 39

(5-Chloro-4-methyl-3,4-dihydro-quinazolin-2-yl)-[2-(1H-imidazol-4-yl)-ethyl]-amine

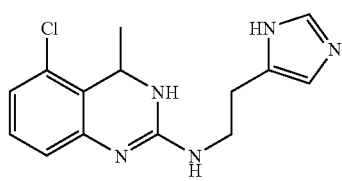

The title compound (MS: m/e=290.1 [M+H⁺]) was prepared in analogy to example 1 from histamine.

Example 40

1-[2-(5-Chloro-4-methyl-3,4-dihydro-quinazolin-2-ylamino)-ethyl]-imidazolidin-2-one

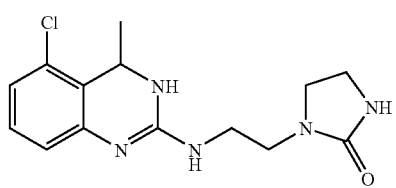

The title compound (MS: m/e=308.2 [M+H⁺]) was prepared in analogy to example 1 from 1-(2-amino-ethyl)-imidazolidin-2-one.

Example 41

(5-Chloro-4-methyl-3,4-dihydro-quinazolin-2-yl)-[2-(1-methyl-pyrrolidin-2-yl)-ethyl]-amine

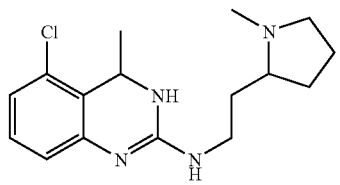

The title compound (MS: m/e=307.3 [M+H⁺]) was prepared in analogy to example 1 from 2-(1-Methyl-pyrrolidin-2-yl)-ethylamine.

Example 42

(5-Chloro-4-methyl-3,4-dihydro-quinazolin-2-yl)-(1-ethyl-pyrrolidin-2-ylmethyl)-amine

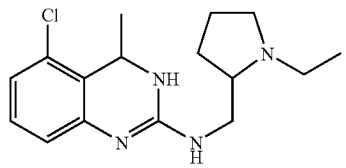

The title compound (MS: m/e=307.3 [M+H⁺]) was prepared in analogy to example 1 from C-(1-Ethyl-pyrrolidin-2-yl)-methylamine.

Example 43

(5-Chloro-4-methyl-3,4-dihydro-quinazolin-2-yl)-[1,4]dioxan-2-ylmethyl-amine

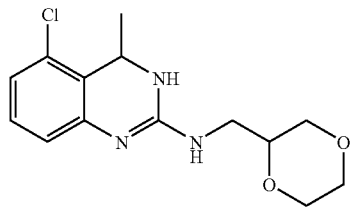

The title compound (MS: m/e=296.2 [M+H⁺]) was prepared in analogy to example 1 from C-[1,4]dioxan-2-yl-methylamine.

The invention claimed is:

1. A compound of formula I

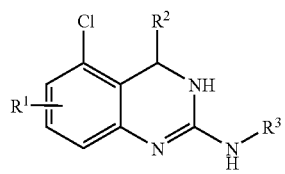

I wherein
$R^1$ is hydrogen or halogen;
$R^2$ is lower alkyl;
$R^3$ is hydrogen, lower alkyl, —(CH$_2$)$_n$-cycloalkyl, —(CH$_2$)$_n$-phenyl optionally substituted by halogen, lower alkyl substituted by halogen, —(CH$_2$)$_n$-heterocyclyl, —(CH$_2$)$_n$N-di-lower alkyl, —(CH$_2$)$_n$NHC(O)-lower alkyl, adamantyl or —(CH$_2$)$_n$—O-lower alkyl; and
n is 0, 1, 2 or 3;
or a pharmaceutically acceptable acid addition salt or tautomer thereof.

2. A compound of claim 1, wherein $R^1$ is hydrogen.

3. A compound of claim 2, wherein $R^2$ is lower alkyl.

4. A compound of claim 3, wherein $R^1$ is hydrogen and $R^2$ is methyl.

5. A compound of claim 4, selected from the group consisting of
5-chloro-4-methyl-3,4-dihydro-quinazolin-2-ylamine,
(5-chloro-4-methyl-3,4-dihydro-quinazolin-2-yl)-methyl-amine,
(5-chloro-4-methyl-3,4-dihydro-quinazolin-2-yl)-cyclobutyl-amine and
(5-chloro-4-methyl-3,4-dihydro-quinazolin-2-yl)-(2,2-difluoro-ethyl)-amine.

6. A compound of claim 1, wherein $R^1$ is halogen.

7. A compound of claim 6, wherein $R^1$ is chloro and $R^2$ is methyl.

8. A compound of claim 7, selected from the group consisting of
5,6-dichloro-4-methyl-3,4-dihydro-quinazolin-2-ylamine,
(5,6-dichloro-4-methyl-3,4-dihydro-quinazolin-2-yl)-methyl-amine,
(5,6-dichloro-4-methyl-3,4-dihydro-quinazolin-2-yl)-(2,2-difluoro-ethyl)-amine, cyclobutyl-(5,6-dichloro-4-methyl-3,4-dihydro-quinazolin-2-yl)-amine,
N-[2-(5,6-dichloro-4-methyl-3,4-dihydro-quinazolin-2-ylamino)-ethyl]-acetamide,
(5,6-dichloro-4-methyl-3,4-dihydro-quinazolin-2-yl)-pentyl-amine,
(5,6-dichloro-4-methyl-3,4-dihydro-quinazolin-2-yl)-(3-methoxy-propyl)-amine,
(5,6-dichloro-4-methyl-3,4-dihydro-quinazolin-2-yl)-[1,4]dioxan-2-ylmethyl-amine and 5,8-dichloro-4-methyl-3,4-dihydro-quinazolin-2-ylamine.

9. A compound of claim 6, wherein $R^2$ is methyl.

10. A compound of claim 1, wherein $R^3$ is hydrogen.

11. A compound of claim 1, wherein $R^3$ is lower alkyl or lower alkyl substituted by halogen.

12. A compound of claim 1, wherein $R^3$ is —(CH$_2$)$_n$N-di-lower alkyl.

13. A compound of claim 1, wherein $R^3$ is —(CH$_2$)$_n$-cycloalkyl.

14. A compound of claim 1, wherein $R^3$ is adamantyl.

15. A compound of claim 1, wherein $R^3$ is —(CH$_2$)$_n$NHC(O)-lower alkyl.

16. A compound of claim 1, wherein $R^3$ is —(CH$_2$)$_n$-phenyl optionally substituted by halogen.

17. A compound of claim 1, wherein $R^3$ is —(CH$_2$)$_n$-heterocyclyl.

18. A compound of claim 17, wherein $R^3$ is piperidin-1-yl.

19. A compound of claim 17, wherein $R^3$ is 2-(1H-imidazol-4-yl) or imidazolidin-2-one.

20. A compound of claim 17, wherein $R^3$ is [1,4]dioxan-2-yl.

21. A compound of claim 17, wherein $R^3$ is 1-pyrrolidin-2-one.

22. A compound of claim 17, wherein $R^3$ is pyridin-3-yl.

23. A compound of claim 17, wherein $R^3$ is 2,3-dihydro-benzo[1,4]dioxin-2-yl.

24. A pharmaceutical composition comprising a therapeutically effective amount of a compound of formula I

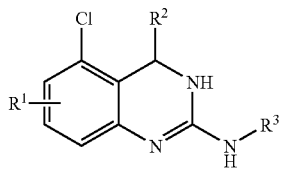

wherein
R¹ is hydrogen or halogen;
R² is lower alkyl,
R³ is hydrogen, lower alkyl, —(CH$_2$)$_n$—O-cycloalkyl, —(CH$_2$)$_n$-phenyl optionally substituted by halogen, lower alkyl substituted by halogen, —(CH$_2$)$_n$-heterocyclyl, —(CH$_2$)$_n$N-di-lower alkyl, —(CH$_2$)$_n$NHC(O)-lower alkyl, adamantyl or —(CH$_2$)$_n$—O-lower alkyl; and n is 0, 1, 2 or 3;

or a pharmaceutically acceptable acid addition salt or tautomer thereof
and a pharmaceutically acceptable carrier.

* * * * *